(12) United States Patent
Kim et al.

(10) Patent No.: US 12,300,387 B2
(45) Date of Patent: *May 13, 2025

(54) ELECTRONIC SYSTEMS AND METHODS FOR THE ASSESSMENT OF EMOTIONAL STATE

(71) Applicant: Next Jump, Inc., New York, NY (US)

(72) Inventors: Yong-Chul Charles Kim, New York, NY (US); Meghan Messenger, New York, NY (US); Greg Kunkel, New York, NY (US); Thomas Fuller, New York, NY (US)

(73) Assignee: Next Jump, Inc., New York, NY (US)

( * ) Notice: Subject to any disclaimer, the term of this patent is extended or adjusted under 35 U.S.C. 154(b) by 3 days.

This patent is subject to a terminal disclaimer.

(21) Appl. No.: 18/336,938

(22) Filed: Jun. 16, 2023

(65) Prior Publication Data

US 2023/0335284 A1    Oct. 19, 2023

Related U.S. Application Data

(63) Continuation of application No. 16/862,114, filed on Apr. 29, 2020, now Pat. No. 11,682,490.
(Continued)

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/0022* (2013.01); *A61B 5/165* (2013.01); *A61B 5/7435* (2013.01); *G06F 16/26* (2019.01)

(58) Field of Classification Search
CPC ...... G16H 50/20; A61B 5/0022; A61B 5/165; A61B 5/7435; G06F 16/26
See application file for complete search history.

(56) References Cited

U.S. PATENT DOCUMENTS 7,124,164 B1   10/2006   Chemtob
8,041,589 B1   10/2011   Blair et al.
(Continued)

FOREIGN PATENT DOCUMENTS

CN    105138222    12/2015
CN    105897551    8/2016
(Continued)

OTHER PUBLICATIONS

Geri Gay, Ph.D. et al., "Pilot Study of Aurora, a Social, Mobile-Phone-Based Emotion Sharing and Recording System," Symposium, Journal of Diabetes Science and Technology, vol. 5, Issue 2, Mar. 2011, pp. 325-332, www.journalofdst.org.
(Continued)

*Primary Examiner* — Sheetal R Paulson
(74) *Attorney, Agent, or Firm* — Fox Rothschild LLP

(57) ABSTRACT

The present invention is directed to an electronic system for the assessment of emotional state. The system allows individual employees to specify their emotions using a set of emojis. The system provides a graphical user interface that displays a list of different emotions and associated emojis that the user can select. The system allows the user to write an entry about his thoughts and emotions in conjunction with the selected emojis and send the message with the emojis to individuals with whom he chooses to share. The system provides a list of company-wide employees from which the user can select. The system receives the messages and implements data structures to process the received messages and produce individual and company-wide emotional state information.

6 Claims, 8 Drawing Sheets

Related U.S. Application Data

(60) Provisional application No. 62/841,180, filed on Apr. 30, 2019.

(51) Int. Cl.
 *A61B 5/16* (2006.01)
 *G06F 16/26* (2019.01)

(56) References Cited

U.S. PATENT DOCUMENTS

| | | | |
|---|---|---|---|
| 9,043,196 | B1 | 5/2015 | Leydon et al. |
| 9,313,177 | B2 | 4/2016 | Blumenfeld et al. |
| 9,652,134 | B2 | 5/2017 | Goossens et al. |
| 10,009,644 | B2 | 6/2018 | Aimone et al. |
| 2004/0179039 | A1 | 9/2004 | Blattner et al. |
| 2010/0153453 | A1 | 6/2010 | Knowles |
| 2010/0235776 | A1 | 9/2010 | Brown |
| 2011/0223889 | A1 | 9/2011 | Stephen et al. |
| 2012/0047447 | A1 | 2/2012 | Haq |
| 2014/0143693 | A1* | 5/2014 | Goossens ............ G06Q 10/10 715/764 |
| 2014/0287387 | A1* | 9/2014 | Vukasinovic ............ G09B 7/02 434/236 |
| 2014/0350349 | A1 | 11/2014 | Geurts et al. |
| 2014/0357976 | A1 | 12/2014 | Pitre et al. |
| 2015/0319119 | A1* | 11/2015 | Ryu ................ G06Q 30/0251 715/752 |
| 2016/0065571 | A1 | 3/2016 | Hoyos et al. |
| 2016/0357402 | A1* | 12/2016 | Matas ................ G06T 11/60 |
| 2017/0046496 | A1* | 2/2017 | Johnstone ............ G06Q 50/01 |
| 2018/0035938 | A1 | 2/2018 | el Kaliouby et al. |
| 2018/0047195 | A1 | 2/2018 | Vissicaro et al. |
| 2018/0218289 | A1 | 8/2018 | Albrecht |
| 2018/0331984 | A1 | 11/2018 | McCall |
| 2018/0373683 | A1 | 12/2018 | Hullette et al. |
| 2019/0007377 | A1 | 1/2019 | Bender |
| 2019/0008466 | A1* | 1/2019 | Shimota ................ G06V 40/20 |
| 2019/0102737 | A1 | 4/2019 | Gudihal et al. |
| 2022/0036481 | A1* | 2/2022 | Curtis .................... A61B 5/16 |

FOREIGN PATENT DOCUMENTS

| | | | | |
|---|---|---|---|---|
| EP | 2940645 | A1 * | 11/2015 | ......... G06F 3/04842 |
| JP | 2017-514194 | | 6/2017 | |
| JP | 2018-139026 | | 9/2018 | |
| WO | 2014068573 | | 5/2014 | |
| WO | 2016/121127 | | 8/2016 | |
| WO | 2017141261 | | 8/2017 | |

OTHER PUBLICATIONS

International Search Report and Written Opinion for International PCT Patent Application No. PCT/US2020/030456, dated Jul. 27, 2020 (12 pages).

* cited by examiner

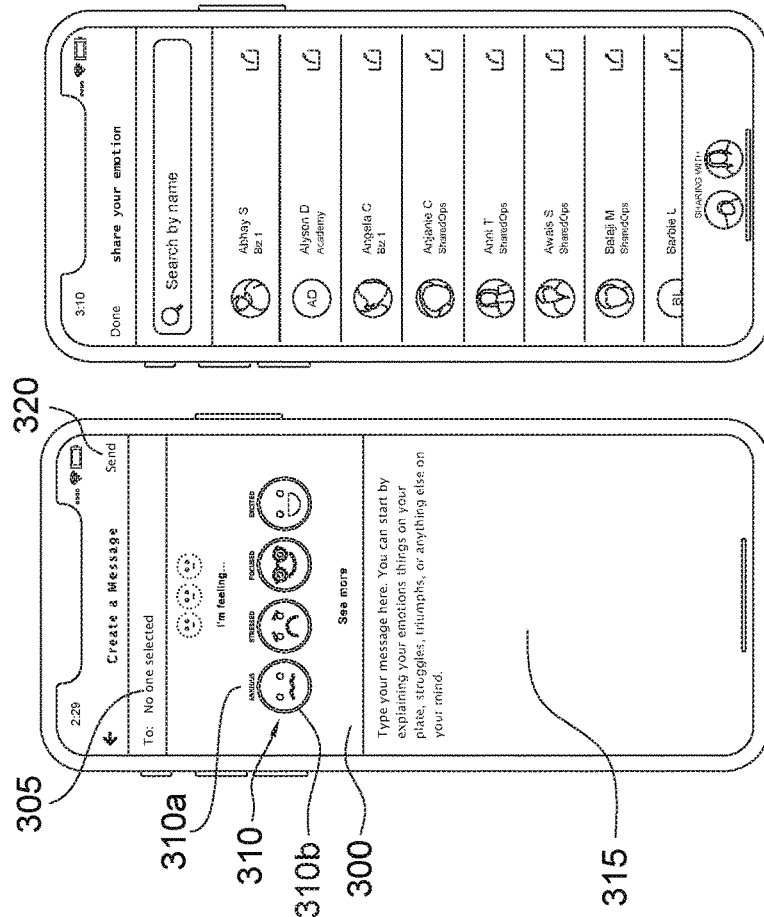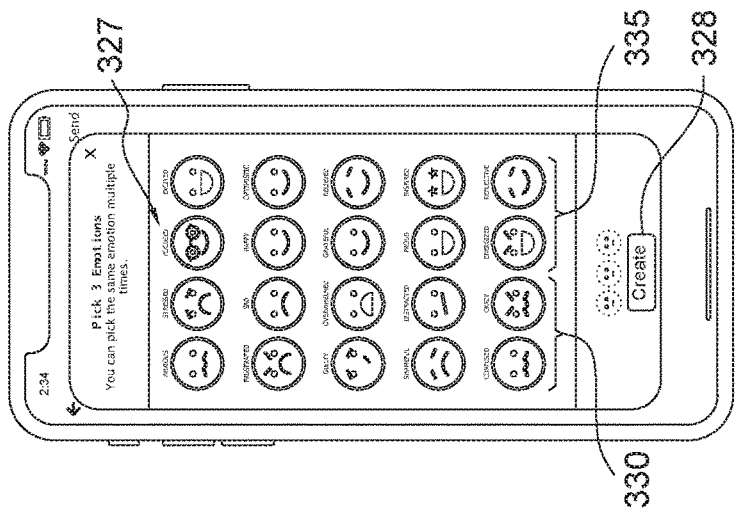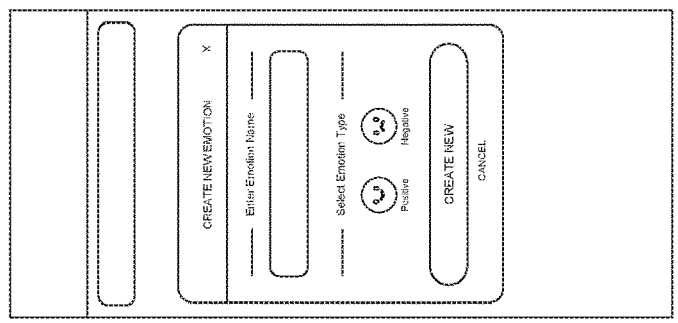
FIG. 3A  FIG. 3B  FIG. 3C  FIG. 3D

ELECTRONIC SYSTEMS AND METHODS FOR THE ASSESSMENT OF EMOTIONAL STATE

CROSS-REFERENCE TO RELATED APPLICATION(S)

This application is a continuation of U.S. patent application Ser. No. 16/862,114, filed Apr. 29, 2020, which claims the benefit of U.S. Provisional Application 62/841,180, filed Apr. 30, 2019, the entirety of which is herein incorporated by reference.

FIELD OF THE INVENTION

The present invention is generally related to the field of human resources technology, including emotional state assessment systems.

BACKGROUND OF THE INVENTION

Employee engagement is a property of the relationship between the organization and its employees. Employee engagement plays a vital role in the overall development of an organization by significantly contributing towards organizational and individual performances. There are techniques available in the art for determining employee engagement. One technique determines employee engagement by detecting the emotional state of a user. Some existing systems for detecting emotional state involve audio or video devices, sensors capable of sensing biometric data, and complex hardware that is specifically implemented to interact with those sensors and analyze the data obtained by those sensors. The devices and sensors, however, are usually installed on the employee's desk and are not portable to be carried with the employee. As such, the employee's emotions outside his office or cubicle cannot be captured, as these systems require the person to be physically present at his desk. For example, an employee's emotion during or after a meeting held in a conference room or a different location cannot be detected. The employee may return to his office to convey his emotion and have his emotion recorded, but the delay may cause him to recollect the event and communicate his thoughts imprecisely. The devices, sensors, and analysis hardware also occupy office space and are expensive to purchase and maintain. Therefore, companies with smaller real estate space and budgets may not be able to afford such solutions.

Some other existing systems for detecting emotional state involve receiving opinions on a business process. The systems receive indications of the emotional states of users interacting with the business process and identify problems of the business process based on the received indication of the emotional states of the users. The systems may include a mobile application or messaging app designed to receive such communication. Such messaging apps, however, fail to adequately and accurately express the user's emotion, mood, or feeling. The business process to which the message is directed may shift the individual to comment on the business process itself, rather than his emotion. For example, the user may type "partner A and associates B and C were discussing issue E with client F. While partner A was talking to client F, associate B appeared to be nervous and associate C appeared to be sad. Associate B should have been more relaxed and associate C should have been happier." This comment provides suggestions to the associates, not the user's emotions. In systems where semantics technology is employed, there may be difficulty in determining who was nervous, who was sad, whether words such as "relaxed" and "happier" refer to emotions occurring in the meeting or suggested by the user, and whether the conveyed emotions are referring to the user's emotions or others' emotions.

The messaging apps may also allow the user to select an expression icon and incorporate the icon into the message itself (e.g., the icon can be inserted after a sentence or between two sentences). This feature, however, is optional and the user can type a message without using any icons. As such, the individual's emotion may not be known. Inserting icons into the message may also raise ambiguity, as the icons may not necessary be tied to the user's emotion. For instance, continuing with the example above, the user may insert an icon representing associate B's nervousness after the word "nervous" and an icon representing associate C's sadness after the word "sad." Using icons in this situation still does not resolve the problems discussed earlier, as they do not reflect the user's emotion. In short, current messaging apps do not provide a way to easily and directly capture a user's emotion that is free of ambiguity.

Additionally, there is very little focus on improving a system or a remote system that works with the messaging apps. Conventional messaging apps emphasize on the user interface appears on the mobile device. The individual can select an expression icon from and type a message in the user interface. There is no known technology that links "emoji" (emotion icon) selection on a message app to the emojis stored on the system behind the app for data aggregation purposes and that determines who has access to the message and the selected emojis. There is no known technology that implements particular data structures for those purposes.

Accordingly, there remains a need for HR technology related to emotional state assessment systems that is improved over the prior art.

SUMMARY OF THE INVENTION

In accordance with principles of the invention, a system for assessment of emotional state is contemplated. The system comprises a mobile device with an emotion journaling application installed. The emotion journaling application configures the mobile device to communicate with an employee database storing a list of employee names of an enterprise and obtain the list of employee names. The emotion journaling application also configures the mobile device to provide a user interface configured to allow creation of an electronic message. The user interface is configured to allow selection of a message recipient from the list of employee names; provide a list of emotion graphical representations; and an option to create an emotion graphical representation and add the created representation to the list of emotion graphical representations. The created representation on the list is available for selection on the mobile device with the emotion journaling application and on other mobile devices with emotion journaling applications.

The user interface is also configured to allow selection of one or more emotion graphical representations or an odd number of emotion graphical representations greater than three from the list of emotion graphical representations; provide a text area allowing a user of the mobile device to input an entry in his own words; make an electronic message transmittable to an electronic message processing system or the selected recipient when at least one message recipient has been selected, three emotion graphical representations have been selected, and a text entry has been inputted, and make an electronic message available to the selected recipient. The selected recipient can access the electronic message through an emotion journaling application on his mobile device. The user interface is further configured present individual, group-wide, and company-wide emotional state information over a period of time based on messages created through the user interface (or the three selections of emotion graphical representations in the messages) and messages created through user interfaces of the other mobile devices with the emotion journaling application (or the three selections of emotion graphical representations in the messages).

The system also comprises an electronic message processing system configured to receive messages created through the user interface and messages created through the user interfaces of the other mobile devices with the emotion journaling application. The electronic message processing system comprises a post data structure configured to convey information in the created message and an emotion icon data structure configured to convey emotion icon-related information (e.g., emotion names and emotion graphical representations). The electronic message processing system also comprises a post and emotion mapping data structure configured to convey emotional state information based information in the post-data structure and information in the emotion-icon data structure. The emotional state information is communicated to the mobile device and used by the emotion journaling application to present individual, group-wide, and company-wide emotional state information over a period of time. The electronic message processing system further comprises a post-access data structure configured to make the electronic message available to the selected recipients based on information in the post-data structure. The post-access data structure is used by recipient's emotion journaling application to make the electronic message available to the selected recipient.

In accordance with principles of the invention, another system for assessment of emotional state is contemplated. The system comprises a mobile device with an emotion journaling application installed. The emotion journaling application configures the mobile device to provide a user interface configured to allow creation of an electronic message. The user interface is configured to allow selection of a message recipient from a list of employee names of an enterprise; provide a list of emotion graphical representations; allow selection of one or more emotion graphical representations; provide a text area allowing user of the mobile device input an entry in his own words; make an electronic message transmittable to an electronic message processing system or the selected recipient when at least one message recipient has been selected, three emotion graphical representations have been selected, and a text entry has been inputted; make an electronic message available to the selected recipient who can access the electronic message through an emotion journaling application on his mobile device; and present individual, group-wide, and company-wide emotional state information over a period of time that includes the three selections of emotion graphical representations in the messages.

The system also comprises an electronic message processing system configured to receive messages created through the user interface. The electronic message processing system comprises a post and emotion mapping data structure configured to convey emotional state information based on information in a database storing electronic messages created through the user interface and information in a database storing emotion icons. The emotional state information is communicated to the mobile device and used by the emotion journaling application to present individual, group-wide, and company-wide emotional state information over a period of time. The electronic message processing system also comprises a post access data structure configured to make the electronic message available to the selected recipients based on information in the database storing electronic messages created through the user interface. The post access data structure is used by recipient's emotion journaling application to make the electronic message available to the selected recipient.

The emotion graphical representations include a group of positive emotion graphical representations and a group of negative emotion graphical representations, wherein each representation in the positive group is associated with a positive numerical value and each representation in the negative group is associated with an equivalent negative numerical value.

Counterpart method and non-transitory computer-readable medium embodiments would be understood from the above and the overall disclosure. Computer-readable medium may be permanent or semi-permanent memory such as hard drive, floppy drive, optical disk, flash memory, ROM, EPROM, EEPROM, etc., as would be known to those of ordinary skill in the art. Computer-readable medium stores computer instructions executable by a microprocessor, and execution of the instructions causes the microprocessor to perform the steps or functions described in this disclosure. Also, broader, narrower, or different combinations of the described features are contemplated, such that, for example, features can be removed or added in a broader or narrower way.

BRIEF DESCRIPTION OF THE DRAWINGS

Various features of examples in accordance with the principles described herein may be more readily understood with reference to the following detailed description taken in conjunction with the accompanying drawings, where like reference numerals designate like structural elements, and in which.

FIGS. 3a-3d depict an illustrative message creating screen of the emotion journaling software application and illustrative screens of the associated lists and options in accordance with some embodiments of the present invention;

DETAILED DESCRIPTION OF THE INVENTION

Embodiments of the present invention are directed to an electronic system for the assessment of emotional state of employees in a company. The company implements the system and provides an app that individual employees can use to specify their emotions using a set of graphical representations (e.g., emojis). The app provides a graphical user interface that displays a list of different emotions and associated emojis that the user can select. Employees are required to select multiple emojis, and they can, for example, select the same emoji three times. The app may require the user to select an odd number of emojis as a way to prevent the user from giving a neutral report (e.g., one happy and one sad emotion, resulting in a neutral). The user writes an entry about his thoughts and emotions in conjunction with the selected emojis and sends the message with the emojis to one or more individuals with whom he chooses to share. The individual can be his mentor or a colleague. The app provides a list of company-wide employees from which the user can select. The app also generates an email version of the message and sends it to the recipient, and conversation can be pursued based on email communications.

The emotions are also stored and made available to the supervisor of the individual's department or a leader of the organization (e.g., CEO). The written information is not shared with that person and is kept confidential. The emotions are provided to that person as an aggregated set of the people in that department or the organization without indicating the identities of those who provided the emotional input. Historical information can be stored and presented in a graphical form to help understand the sense of the individual, group, or company-wide emotional state over time.

The user can also view the historical information about his input into the app, but the app may be configured to condition such access on the user having created and sent a certain number of messages during a particular time period (e.g., 30 days). This and other features provide a gamification experience that can motivate employee participation and engagement with the app.

The app is configured to indirectly develop and train an individual to be a better decision maker. The app uses the concept that a person's decision making follows his emotions. Being self-aware and practicing being in touch with his emotions such as twice a week at the minimum will make the individual a better decision maker. When individuals are aware of their own emotions and their closest team member emotions, the team performs better.

Figure 1:
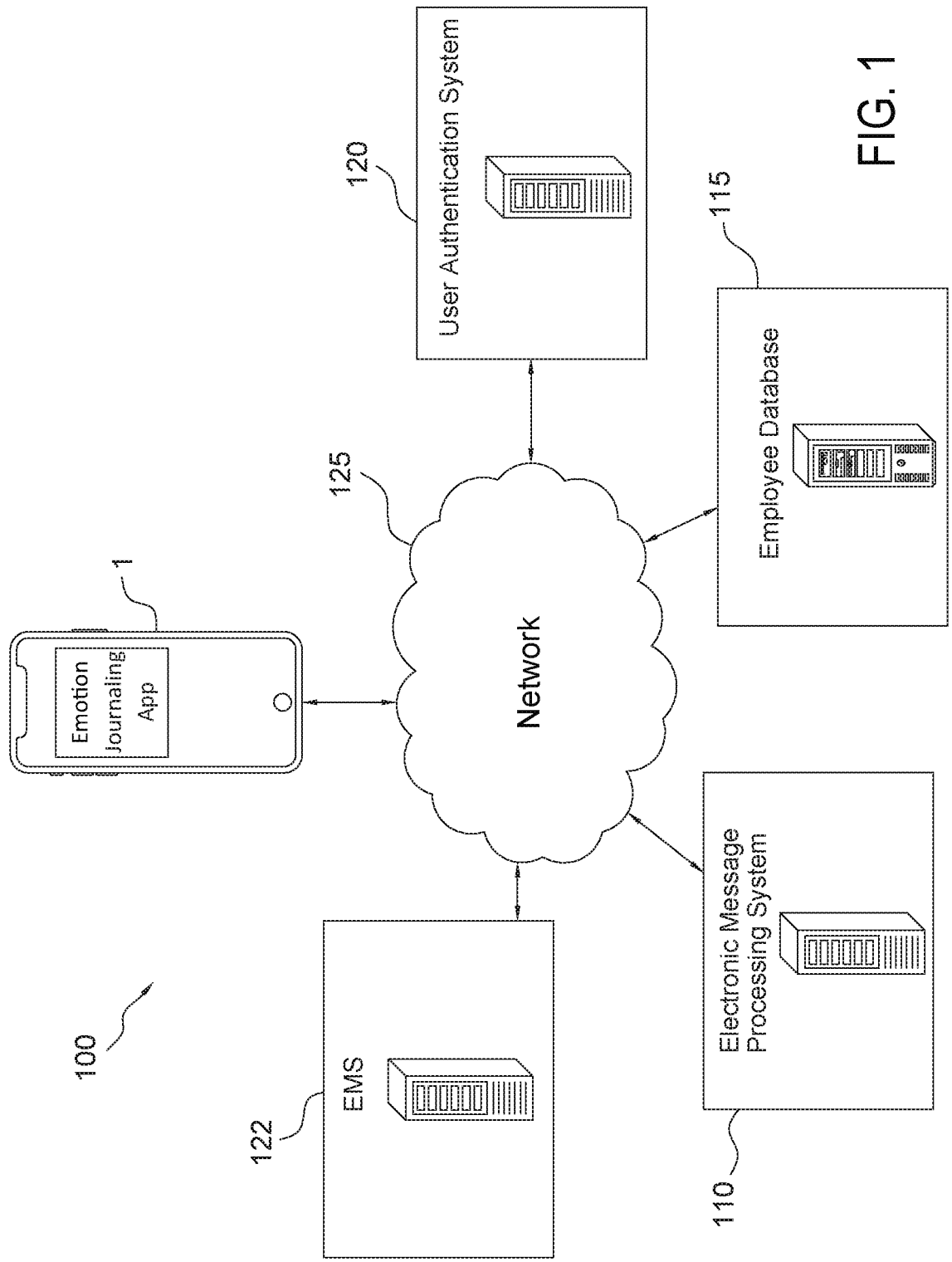
FIG. 1 depicts an illustrative system for the assessment of emotional state in accordance with some embodiments of the present invention.

FIG. 1 depicts an illustrative system 100 for the assessment of emotional state. The system 100 comprises an electronic device 1 with an emotion journaling software application (the "emotion journaling application" or simply, the "application") that configures the device to generate an electronic message, an electronic message processing system 110, an employee database 115 configured to store employee identity information of an enterprise, a user authentication system 120, and an email management system ("EMS") 122. The device, systems, and database 105, 110, 115, 120, and 122 can transmit and receive data over a communications network 125 such as the Internet and they include the necessary hardware and software that supports communications over the network.

FIGS. 2-6 illustrate part of the user interface of the emotion journaling application. The discussion of FIGS. 2-6 may also involve FIG. 1. The application is installed on the electronic device 1. FIG. 2 depicts a login screen 210 of the application. An employee can enter his company sign-in credentials from the login screen 210 through the electronic device 205 and the entered information is transmitted over the network 125 (FIG. 1) to the user authentication system 120 (FIG. 1) by the electronic device 205. The sign-in credentials include information that identifies that the user is an employee of the company, such as an email address based on the company's email domain, employee identification number, or other employee identifiers. Upon receiving the credentials, the authentication system checks if they (e.g., an email address and password) match the credentials stored in the authentication system (e.g., the email address and password pre-stored in the authentication system). The credentials stored in the authentication system, for example, may be created and stored in the authentication system when the person joins the company and the human resources department of the company creates an email address and password for that person through the company's computer system. The credentials stored in the authentication system can be updated when the user changes his credentials (e.g., password). The authentication system is configured to store sign-in credentials of the employees hired by the company.

If the entered credentials and the stored credentials match, the user is then granted access to the emotion journaling application. Additionally, the authentication system generates an electronic authorization or security token and sends it over the network to the electronic device. The emotion journaling application incorporates the token into all of its communications with the electronic message processing system and employee database. The token is required to communicate with those systems and database and is checked and verified by those systems and database before the emotion journaling application can access the functionalities and data provided by those systems and database. The emotion journaling application and the authentication system perform a user authentication process to allow the user to access the application, the electronic message processing system, and the employee database.

This authentication implementation is configured to use the authorization token to enable access to services offered on the enterprise network of that company or by the enterprise employing that user to gain access to the services (e.g., to all other services or to join the enterprise network and have access to enterprise applications such as the emotion journaling application and electronic message processing software application). This process provides efficiency in that the user, or the system implementing each enterprise application, does not require separate logins for each of the enterprise's software applications on the user's mobile device to access corresponding services. At the same time, this process also establishes highly secure inter-system relationships and connections, such as trusted connections using communications and security protocol, based on identity authentication and security tokens to ensure that unauthorized individuals or individuals outside the enterprise do not have access to the enterprise applications. This security implementation provides a simplified authentication process or one single authentication process that can simultaneously verify that the user is an employee of the company and allow the user to access all enterprise applications on the enterprise network. In contrast, conventional systems require a separate authorization process for each procedure, such as an authentication process for verifying whether the individual is an employee, a separate authentication process for granting access to one of the enterprise applications after verifying that the individual is an employee, another separate authentication process for granting access to another one of the enterprise applications after verifying that the individual is an employee, and so forth.

The authentication system limits users of the emotion journaling application and access to the electronic message processing application and other services on the enterprise network to only employees or authorized members of the company.

The above authentication processes and systems (and the anonymization processes and systems discussed below), for example, can be those described in application No. 62/807,693, the entirety of which is incorporated by reference. Other processes, systems, and features described in that application may also be adopted by or be used in conjunction with the electronic systems and methods for the assessment of emotional state.

FIG. 3a depicts an illustrative message creation screen 300 of the application. The message creation screen 300 provides an interface that presents or consists essentially of an option 305 to select one or more message recipients, an option 310 to select multiple emotions or emotion graphical representations from a list containing different emotion names 310a and associated emotion representations 310b, a text area 315 to enter writing using text entry, and an option 320 to send a message. The interface may have only or substantially only the text entry area (e.g., freestyle text entry) and the two options to select message recipients and emotion/emotion representations.

Option 305 to select one or more message recipients is configured to select one or more employees of the enterprise. The electronic message processing system (FIG. 1, 110) is configured to communicate with the employee database (FIG. 1, 115) and obtain employee identity information from the employee database. Employee identity information may include names of employees and an identifier for each employee to be used by the processing system for making the message available to the appropriate person. For example, upon selecting "Michael" from option 305, the processing system determines that "Michael" is associated with identifier "0020" and presents the message to identifier "0020" so that Michael can view the message. The identifier may be an internal identifier used by the processing system and employee database to identify an employee. This identifier may be referred to as a recipient identifier. The emotion journaling application communicates with the processing system to obtain the employee identity information and make employees listed in the employee identity information available for selection through option 305. An update to the employee database also updates the employee list in option 305 accordingly. In some embodiments, the emotion journaling application may be configured to communicate with the employee database to obtain the employee identity information or the employee list directly. Option 305 may only be configured to select employees of the enterprise and may not be integrated with the user's personal contacts on his mobile device. The emotion journaling application has a separate, different contact that is provided by the processing system (or the employee database). FIG. 3b depicts an illustrative list of employees that can be selected. Employees on the list are also individuals who have access to the emotion journaling application. If the employee has not installed the application on an electronic device using his sign-in credentials, then the message sent to him is saved on the electronic message processing system and the employee can view it after he installs the application. In embodiments, the list may not show individuals who have not yet installed the application (only those who have the application installed are shown).

The list includes different human emotional states or emotion names (e.g., happy, sad, focused, stressed, and the like) and each is associated with an emotion graphical or pictorial representation. Emotion graphical representations can be emojis, emoticons, or other forms of facial expressions. Emojis are actual pictures showing a facial expression (e.g., a small digital image or icon used to express an emotion), instead of typographics. Emoticons or typographics are pictorial representations of a facial expression using typographic characters, such as punctuation marks, numbers, and letters, to express a person's feelings or mood (e.g., :-), :-(, :-D, etc.). FIG. 3c depicts an illustrative list 327 of emotions that can be selected. FIG. 3c also depicts an option 328 to create additional emotion representations that are not on list 327.

In the creation process as shown in FIG. 3d, the emotion journaling application may provide an option to enter a name of the emotion, an option to select an emotion type (e.g., positive or negative), and an option to select one of the pre-created emotion representations or emojis. The created emotion representation is transmitted to the electronic message processing system and the electronic message processing system updates list 327 by adding the newly created emotion representations into the list. The electronic message processing system then communicates the updated list to the emotion journaling application and other emotion journaling applications. The update is communicated to the emotion journaling application and other emotion journaling applications as soon as the user creates the emotion representation, or in real time. The new graphical representation then appears on the list and is available for selection by the user and other users during message creation. In some embodiments, the new graphical representation is organized or displayed as one of the top level or core emotions (e.g., sadness, anger, happiness, etc.), as opposed to a lower level or secondary emotion (e.g., an emotion under the sadness emotion, an emotion under the anger emotion, or an emotion under the happiness emotion, etc.). The user interface can be configured to require that the user categorizes the new emotion under one of a set of core emotions. In some embodiments, the emotions can be displayed and selected using emotion names or text only, such as displaying the word "happy" and making the word "happy" selectable.

Option 310 is a dedicated option or field (separate from the text area 315) where the user can select or enter his emotions. The selected or entered emotion graphical representations appear in this dedicated field only and are not shown in the text area 315. Option 310 is a field that allows emotion graphical representation selection only, i.e., it is without the option to receive text entry (other than in the new emotion creation step, where the user can enter an emotion name).

The emotion journaling application is also configured such that multiple emotion graphical representations must be selected before the message can be sent to the recipient. Preferably, three emotion graphical representations or an odd number of emotion graphical representations should be selected. The emotion journaling application is also configured such that the same emotion name or emotion graphical representation can be selected more than once. The order in which the emotion graphical representations are selected is also recorded. In some embodiments, the odd number may also be one, although this is not preferred. Each of the emotions or emotion graphical representations is further associated with a numeral value, in particular with either a positive value (e.g., +1) or an equivalent negative value (e.g., −1). The emotion graphical representations include a group of positive emotion graphical representations 330 and a group of negative emotion graphical representations 335. Each of the representations in the positive group 330 is associated with a positive value, whereas each of the representations in the negative group 335 is associated with an equivalent negative value. Each of the representations in the positive group 330 may have a first color (e.g., green), while each of the representations in the negative group 335 may have a second color different from the first color (e.g., red). The emotion journaling application can be configured to only display positive emotions in one color (or color theme), such as green, and all negative emotions in one color (or color theme), such as red. The numerical association in combination with the odd number selection returns a total value that is strictly either positive or negative. The total value is calculated by adding all associated values of the selected emotion graphical representations (e.g., adding +1, −1, and +1 equals +1, adding +1, +1, and +1 equals +3, etc.). The calculation can be performed by the electronic message processing system after the message is transmitted to that system. For emotion representations created by the user, the selection of the emotion type assigns that representation a corresponding positive or negative value that can be used for calculation.

The text area 315 is a field allowing the user to compose a message in his own words. In particular, the text area 315 is a field where the user writes to describe his emotions, feelings, moods, thoughts, and/or explanation for the selected emotion graphical representations. The text area 315 is an area where the user can write by typing on a QWERTY keyboard of the electronic device. The user may also write in other ways, such as by speaking to or using gestures to convey his words to the electronic device. The text area 315 is a field configured to receive and display text only, i.e., without the option to display emotion graphical representations.

The send option 320 is configured to transmit a message (including specified emotions) upon selection only after the user completes all three fields 305, 310, and 315 (e.g., selects at least one message recipient, at least three emojis, and enters a written message). If the user completes only one or two of the three fields, then the send option 320 is disabled and the user will not be able to send the message (and specified emotions). The term "message" may refer to an electronic message with at least one message recipient selected, only an odd number of emojis selected, and a written message in the text area. After the user creates a message (e.g., with at least one message recipient selected, only an odd number of emojis selected, and a writing in the text area), the user can select the send option 320 to send the message, which includes the selected emotion representations and the written message, to the recipient. The time the message is created (i.e., when the user selects the send option 320) is also recorded by the emotion journaling application.

The message, which includes at least one message recipient selected, only an odd number of emojis selected, and a written message in the text area, is transmitted to the electronic message processing system. The electronic message processing system processes the message and makes the selected emotion representations and the written message available to the recipient for viewing. Only the selected recipients can view the message in its entirety; none of the other users or employees using the emotion journaling application can access that message (e.g., that message is available on the recipient's emotion journaling application only). The recipient can only view the message (the selected emotion representations and the written message) from the emotion journaling application installed on his mobile device, into which he needs to login (see login and authentication processes described above) if he is not already logged in or has been logged out in order to use the application. The time information may also be transmitted to the electronic message processing system so that the electronic message processing system or the recipient's emotion journaling application can use that information to arrange the messages in chronological order or other order based on time.

The user can create and send a message whenever he feels like and for whatever reason he wants after he logs into the emotion journaling application. The ability to create and send a message is not restricted by the emotion journaling application after the user is authenticated by the authentication system. The gamification aspect of the application does not limit the user's ability to compose a message, because message creation is a basic function that is required to unlock access to other services and information in the application. The ability to create and send a message is not tied to an event or condition, such as requiring an event to happen first and then conveying an opinion or emotion about that event (or conveying an opinion or emotion while the event is happening). The application is directed to communication between employees and the discussion can be anything they wish to discuss. The user can create and send messages freely.

Figures 4A, 4B, 4C:
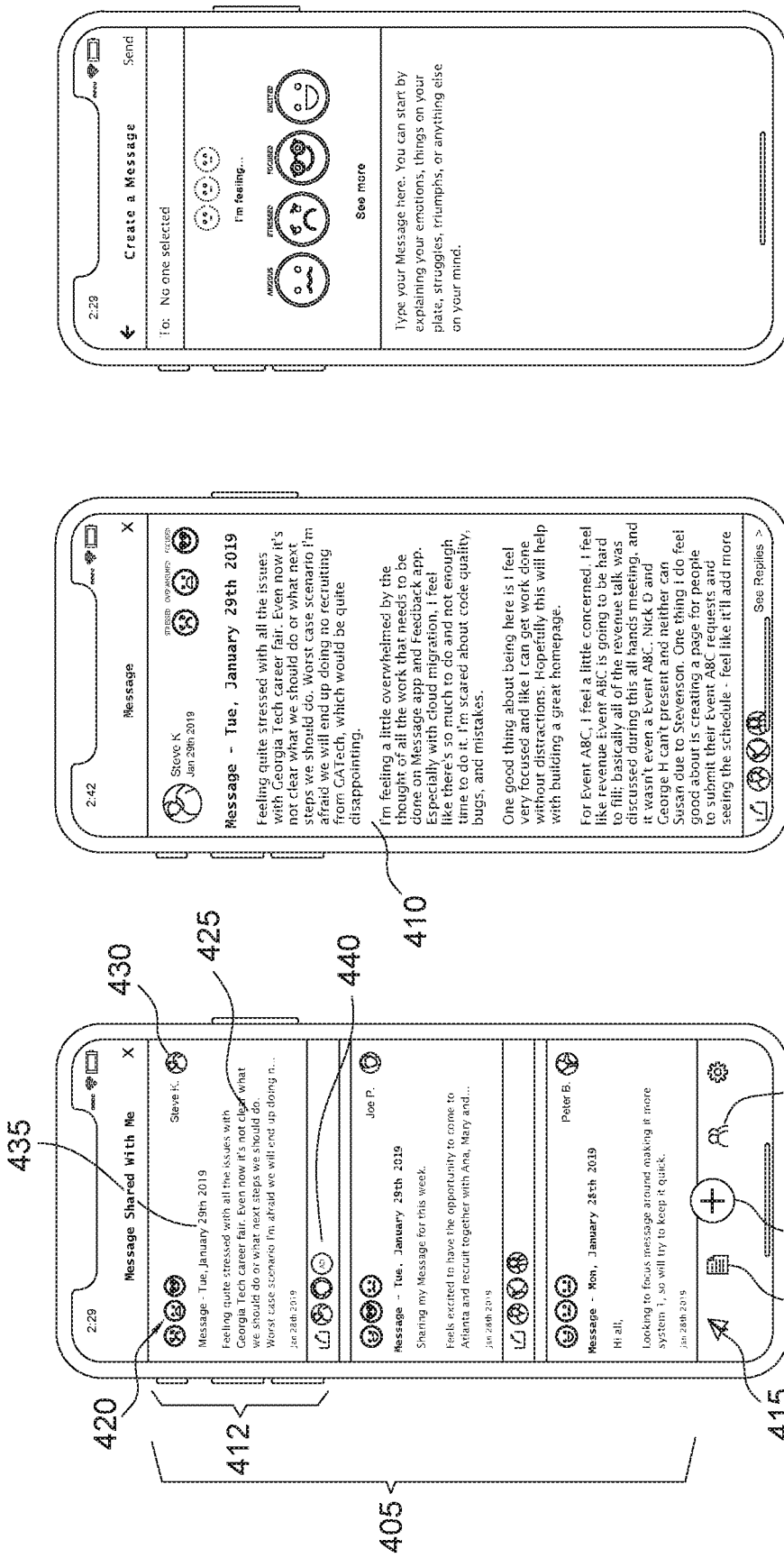
FIGS. 4a-4c depict illustrative message viewing screens of the emotion journaling software in accordance with some embodiments of the present invention.

FIGS. 4a-4b depict illustrative message viewing screens 405, 410 of the emotion journaling application. The first or main message viewing screen 405 shows a list of messages that the user or recipient has received. The emotion journaling application provides an option 415 that can be selected to view the list 405. Each message 412 shown on the list 405 may also display its corresponding emotion representations 420, emotion description 425, sender 430, message sent/creation date 435, and other message recipients 440 (the user can select multiple message recipients and those recipients other than the user are shown here). The portion designated by 435 may also be referred to as the title of the message. For example, the title 435 may have a format "Message—[date of when the message was created]." Screen 410 and message 412 show illustrative actual messages seen by the user. The emotion representations 420 are displayed in the order in which they were selected. When a user logs into the emotion journaling application, the entered sign-in credentials (e.g., company email address or employer ID number used in the user name field) may be used, or the entered sign-in credentials may be associated with an identifier in the employee database that is used by the electronic message processing system to identify the user, so that the electronic message processing system knows who the sender is when that user sends a message. This identifier may be referred to as a user identifier or sender identifier.

The emotion journaling application also provides an option that can be selected to view each message 412 in detail. FIG. 4b depicts a second or detailed message viewing screen 410 after that option is selected. The emotion journaling application also provides an option 445 that can be selected to view messages that the user has sent. Selecting option 445 may display screens similar to screens 405, 410 except that the information in those screens are tailored to messages that have been sent by the user. The emotion journaling application also provides an option 445 that can be selected to bring up the message creation screen shown in FIG. 4c or FIG. 3a.

Figures 2A, 2B, 2C:
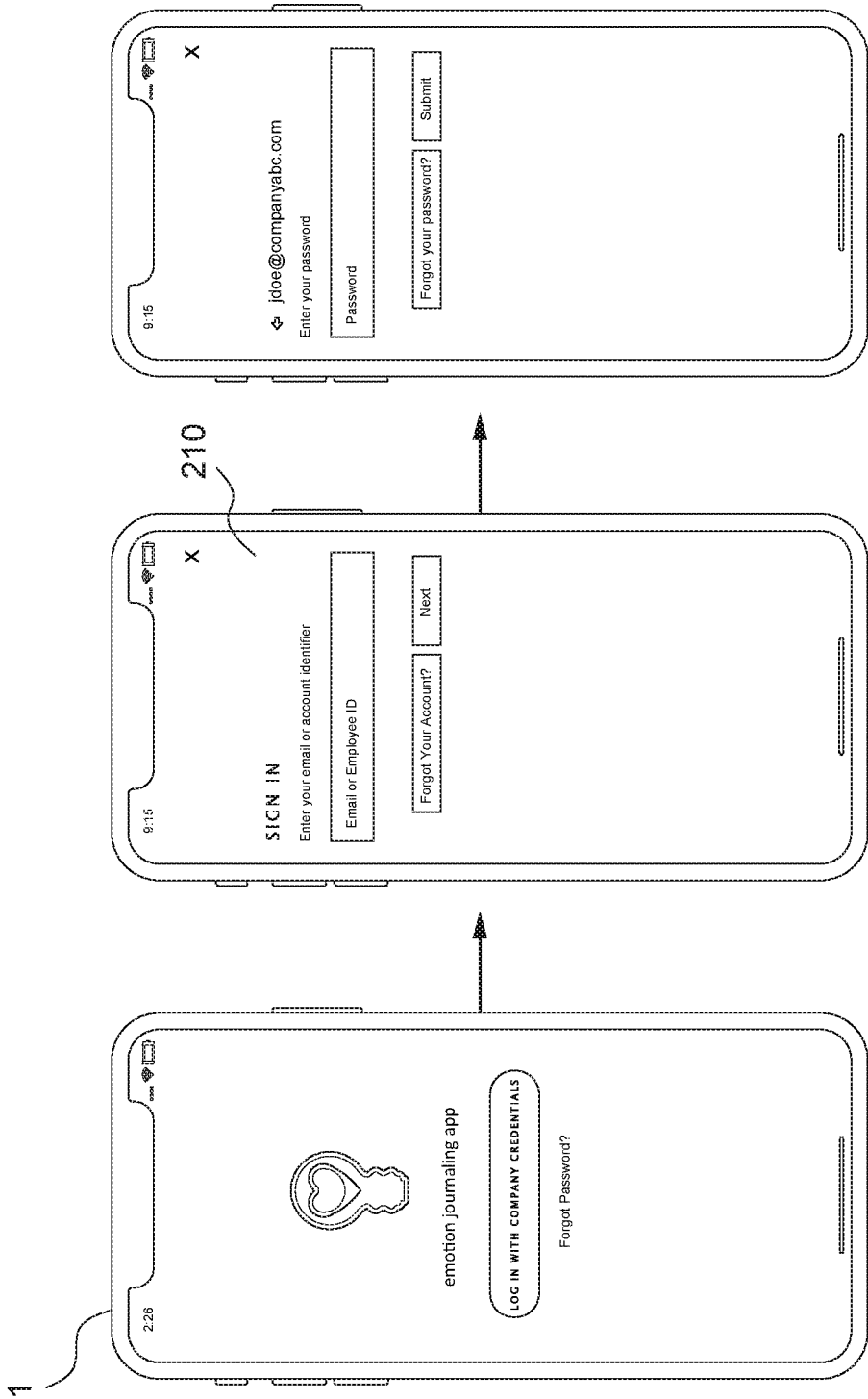
FIGS. 2a-2c depict illustrative login screens of the emotion journaling software application in accordance with some embodiments of the present invention.

The electronic device or device 1 in FIGS. 2A-2C, is preferably a handheld mobile phone. The emotion journaling application is preferably a mobile application or mobile app configured to be installed on the mobile phone. Therefore, composing and sending a message through the mobile phone or mobile app is the preferred method of sending a message. This method makes it harder to go back and edit the message compared to other platforms such as email and promotes visceral thinking rather than analytical thinking.

Figures 5A, 5B:
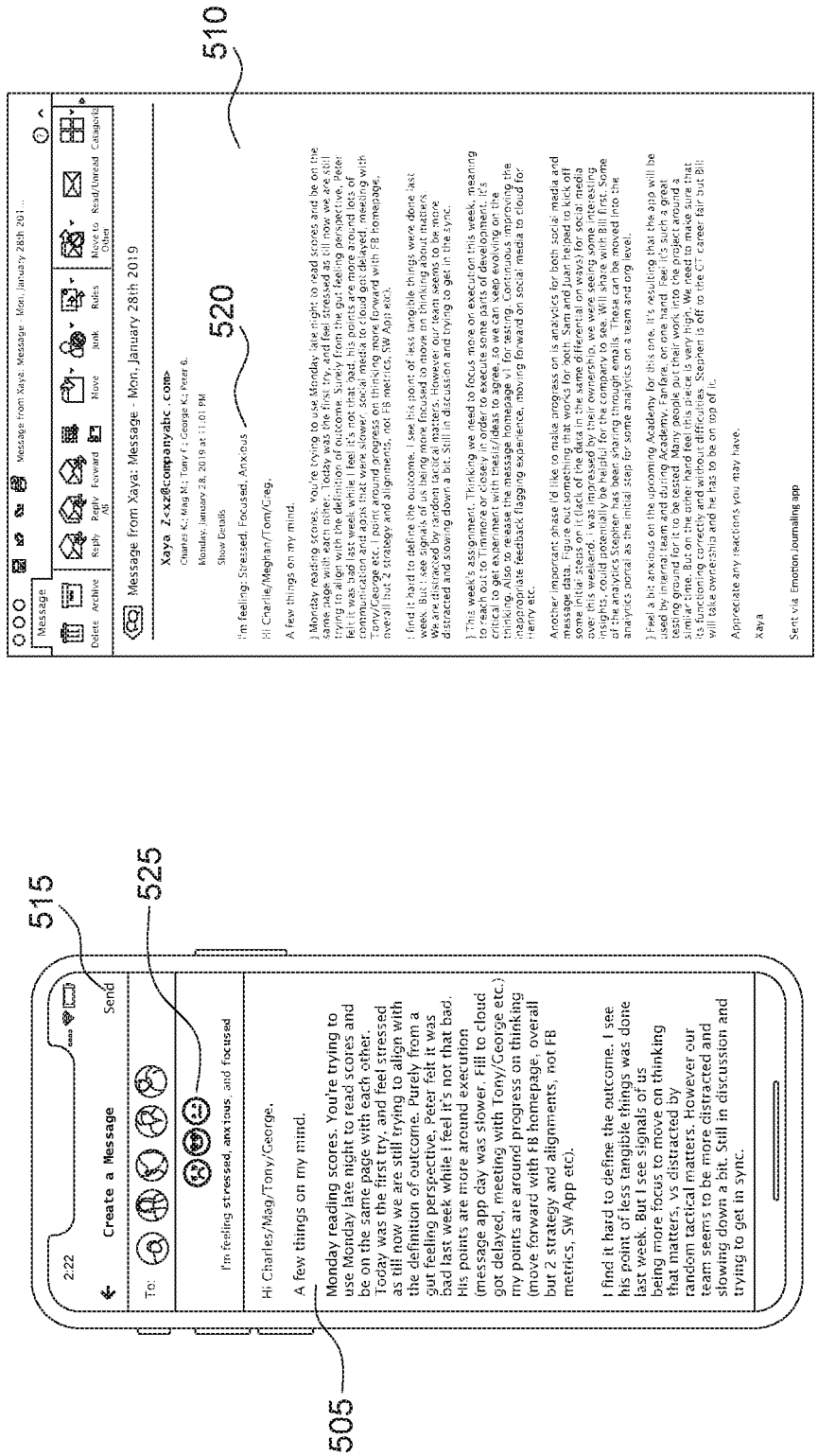
FIGS. 5a-5b depict an illustrative message created on the emotion journaling application and an illustrative email version of the message in accordance with some embodiments of the present invention.

In response to the user sending the message, the system 100 for the assessment of emotional state also generates an email containing the selected emotions and emotion description and sends it to each selected recipient. The email is sent to the company email address of the recipient. The generation and transmission of email is facilitated by the EMS 122. The EMS 122 is a conventional EMS that is known in the art. The recipient identifier is used to determine the corresponding email address (they may be linked by the system 100). The recipient can then view the email or an email version of the message through his company email account. The email may show the actual emojis selected or the emotion names. FIGS. 5a-5b show a message 505 created on the emotion journaling application (with all three fields completed) and an email version 510 of the message generated in response to the user selecting "send" 515. The email 510 shows the selected emotions in text 520 (or with their emotion names), rather than the actual emojis 525. The sender and recipients can communicate over email regarding that message in addition to using the emotion journaling application.

The emotion journaling application provides an option 450 (FIG. 5) that can be selected to view historical information in a graphical form that helps provide a sense of the individual, group, or company-wide emotional state over time. FIG. 6a depicts an illustrative historical emotional state information screen 600 showing an emotional state graph 605 and other information 610, 615 (615a and 615b), and 620. FIG. 6a is also a depiction of the historical information about the user's input into the emotion journaling application.

Emotions selected by the user (including the emotion name, graphical representation, and numerical value) are stored and tracked by the electronic message processing system. These storing and tracking processes may occur when the electronic message processing system receives the message from the emotion journaling application. Recipients selected and the user's written messages may also be stored and tracked by the electronic messaging processing system. In some embodiments, with respect to the selected emotions, the electronic message processing system may store and track only the numerical value of the selected emotions. The emotion name and graphical representation may be ignored by the electronic message processing system. The electronic message processing system is configured to track the numerical values, such as the sum of those values on a daily basis and over a period of time, and the emotion journaling application is configured to present the tracked numerical values, such as in a graphical form, to help provide a sense of the individual, group, or company-wide emotional state over time. The time when the message is sent is used to build the graphical representation. Diagram 605 is such a graph. The tracked numerical values are helpful to understand whether the user's emotional state has been positive or negative or the trend of his emotional state. A larger positive sum may indicate that the user's emotional state is more positive (e.g., optimistic, hopeful, confident, happy, and the like) whereas a larger negative sum may indicate that the user's emotional state is more negative (e.g., pessimistic, hopeless, fearful, unhappy, and the like).

The electronic message processing system can also be configured to track the ratio between the number of positive emotions and the number of negative emotions that the user has entered. The emotion journaling application is also configured to present this information in a graphical form. For example, diagram 610 shows that 65% of the user's selected emotions are negative emotions and 35% of the user's elected emotions are positive emotions. The electronic message processing system and the emotion journaling application can also track and display a similar ratio based on emotion selections aggregated from employees in the same department as the user and a similar ratio based on emotion selections aggregated from everyone in the company.

The electronic message processing system can also be configured to track the number of messages that the user has been given in a time period 615a, store a default number indicating the number of different messages (e.g., with different written content and/or emotion selections) that the user should be given in a time period 615b, and track the number of misses if the user fails to send at least the specified number of messages 615b. All that information can be communicated by the emotion journaling application to the user. For example, the screen 600 shows that the user has written five messages in the past 30 days. The screen 600 also shows that the default number is two in a one-week period. If the user submits fewer than two messages per week, then that incompletion may count as a miss. Adhering to a schedule requiring the user to send a threshold number (e.g., two) of messages in a time period (e.g., a week) can help the user build up a habit of conveying his emotion regularly. The emotion journaling application or the processing system is configured to build that habit by way of interaction with the user, such as those illustratively described herein. Information 615b shows that the user has three misses, which may mean that the user failed to submit at least two messages a week for three consecutive or nonconsecutive weeks.

The emotion journaling application provides an option 620 to present the emotion trend 605, emotion ratio 610, and emotion stats 615 over different time periods, such as 30, 60, or 90 days, and the information or graph in the emotion trend 605, emotion ratio 610, and emotion stats 615 will be updated accordingly based on the selection. The screen 600 shows that all the displayed information is based on the past 30 days.

The user can view the historical information about his input into the emotion journaling application, but the application may be configured to condition such access on the user having created and sent a certain number of messages during a set time period. For example, before the user can view the screen 600 with the emotion trend 605, emotion ratio 610, and emotion stats 615 information for the first time, the application may require the user to create and send at least three messages. After that, the user may be granted access to the information in the screen 600 over a 30-day period. As time progresses, access to the same information over a 60-day period may require the user to create and send three additional messages after the 30-day period. This system of unlocking the screen 600 and subsequent information is provided as a gamitication feature that helps encourage employee participation and engagement with the emotion journaling application, or encourages employees to convey their emotions and engage in such behavior in a consistent manner. This system may also be used to unlock access to other information in the application.

Figure 6B:
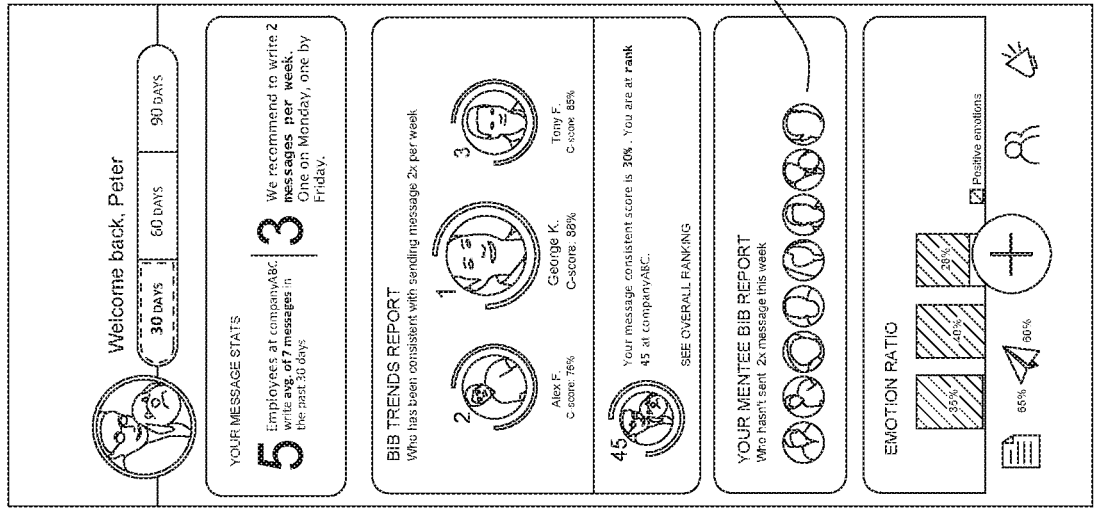
FIG. 6b depicts an illustrative screen of the emotion journaling application showing other information that can be stored and tracked by the electronic message processing system in accordance with some embodiments of the present invention.
Figure 6A:
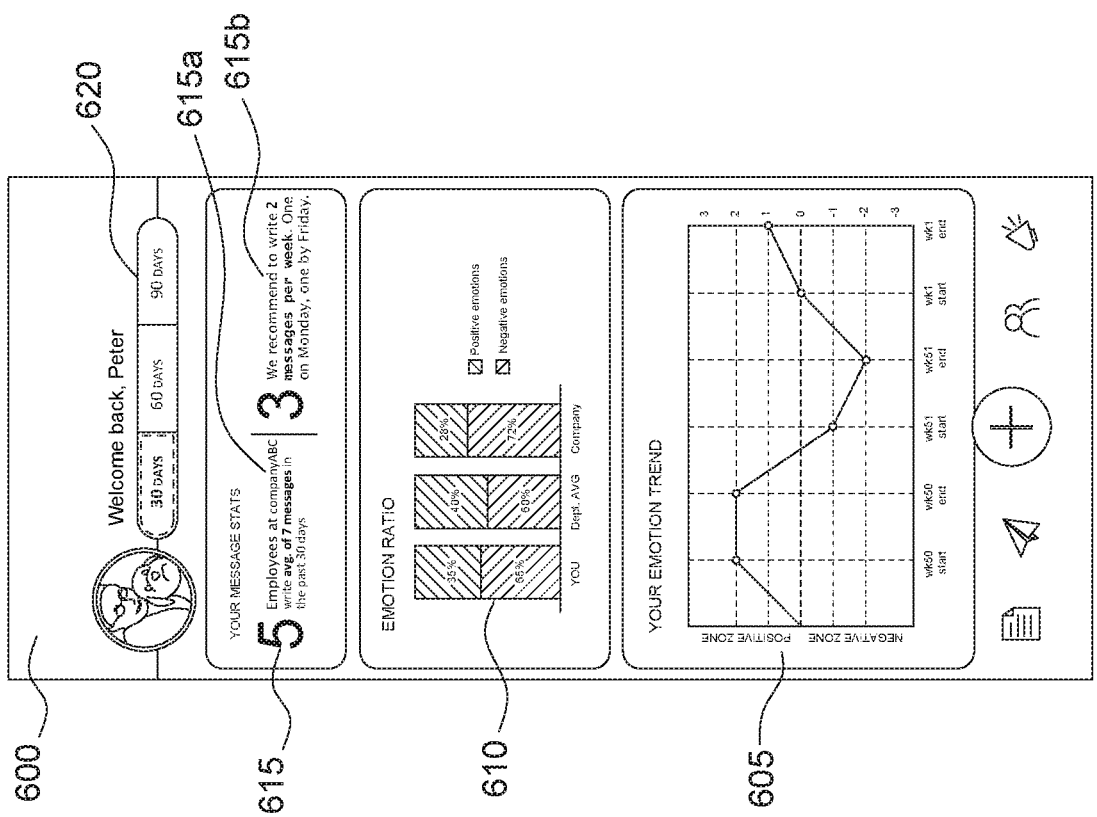
FIG. 6a depicts an illustrative historical emotional state information screen of the emotion journaling software in accordance with some embodiments of the present invention.

FIG. 6b depicts an illustrative screen of the emotion journaling application showing other information that can be stored and tracked by the electronic message processing system. For example, the electronic message processing system and the emotion journaling application can track who in the group has not yet sent the specified number of messages required in the time period and can convey that information to the user or group leader (625). A supervisor or administrator version of the emotion journaling application may be provided and configured to offer such functionality.

Figure 7:
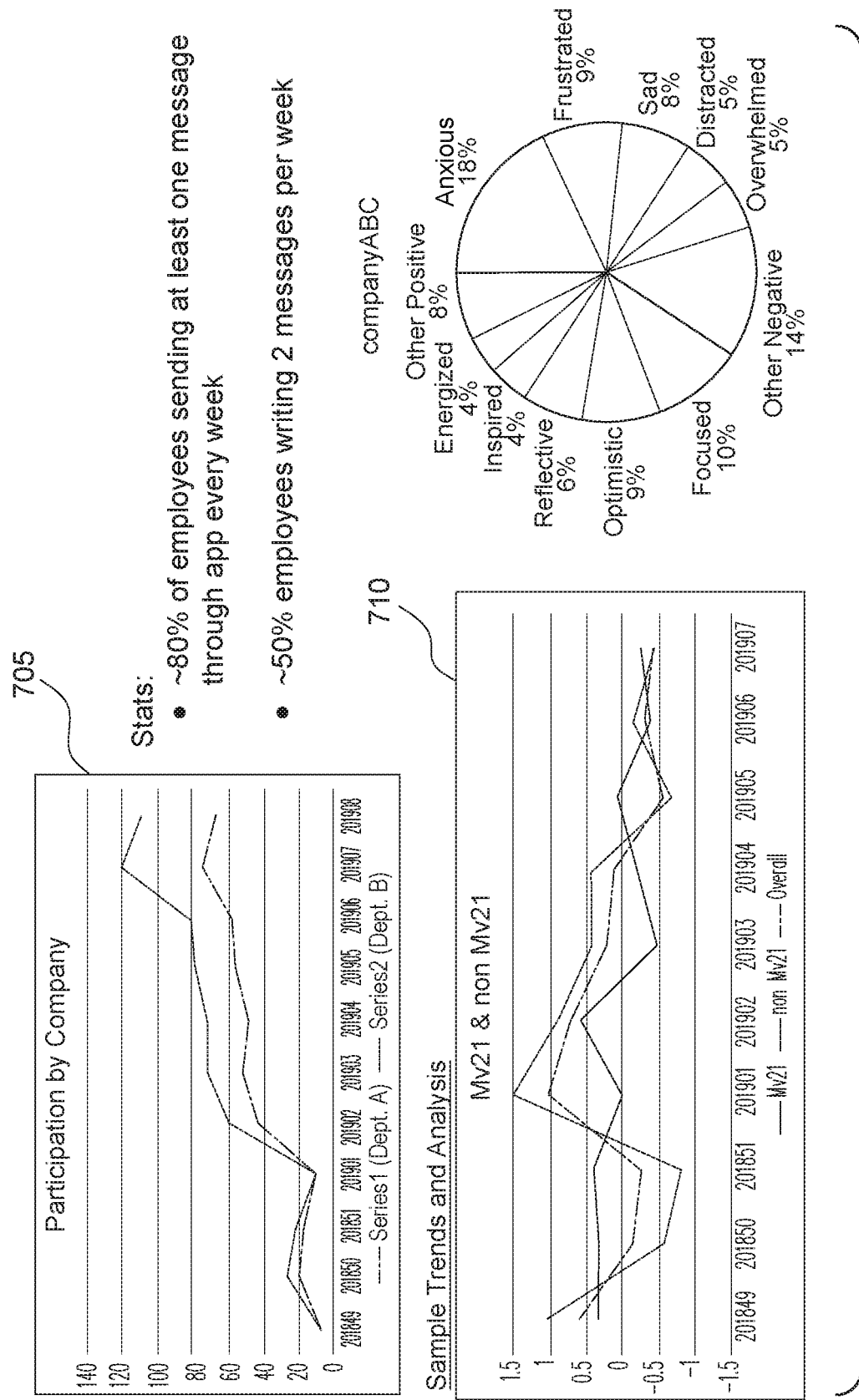
FIG. 7 depicts other illustrative information that can be tracked and communicated by the electronic message processing system and the emotion journaling application in accordance with some embodiments of the present invention.

For another example, as shown in FIG. 7, the electronic message processing system can track company-wide employee participation 605 (referring to employee participation in using the emotion journaling application), company-wide emotion trend 710, and department-wide or company-wide aggregated emotion selections 715, all of which can be presented by the emotion journaling application such as in the screen 600. FIG. 7 is also a depiction of the historical/aggregated information about all employees' input into the emotion journaling application.

All that information may be made available to the supervisor version of the emotion journaling application so that only the group leader or other higher ranked company officials can view such information. The supervisor version of the emotion journaling application may include access to company-wide and/or department-wide information, in addition to the user's information. In some embodiments, this version of application may also view each emotional input and its sender information, even if the user or leader of this version was not selected as a recipient by the sender. From diagrams such as 705 and 719, the supervisor can see when teams' emotion or sentiment is changing, e.g., going up, going down, or staying the same.

The employee version or non-supervisor version of the emotion journaling application may be one that has access to the user's information only (no access to company-wide information, except emotion ratio information 605).

The historical or aggregated information, whether it is the information of the individual, the group, or the company, is based on emotion selections or only emotion selections made through the emotion journaling application. The written content (the written message in the text area), recipient information (or recipient identities), sender information (or sender identifier) are saved on the electronic message processing system but are not used in producing such information. The written content, recipient information, and sender information are included and used when the user sends the message to the recipient and in generating and sending the email. The historical or aggregated information is also produced in real time in the emotion journaling application as employee input is received. Aggregation can be performed on an individual level, group level, or company-wide level.

The emotion journaling application is also configured to send reminders or notifications, whether in the emotion journaling application or through email. In some embodiments, the notifications are generated based on the default number of messages that the user should create and send in a set time period, and the number of messages that the user has created and sent before the time period expires. When the number of messages that the user has created and sent before the time period expires is less than the default number (e.g., two), a reminder is sent. The reminders are sent before the time period expires. The notifications are used to inform the user that he has not created and sent enough messages to peers in that time period. The notifications may be provided by the emotion journaling application such as through push notification, a pop-up window, sound, or vibration, or by the system or EMS sending an email with the reminder.

In one embodiment, the processing system is configured to send alerts and determine whether the user is following a certain procedure and rules, such as entering at least two messages per week. When the processing system determines that the user is not compliant, it can prevent or restrict the user's rights or access to the emotion journaling application or other resources such as apps or systems supported on the enterprise network. For example, the user will be blocked from viewing content in the emotion journaling application (e.g., FIGS. 6A-6B) of the user or some other apps or systems if the two-message per week requirement has not been satisfied. In this process, the emotion journaling application may send a message or command to another system within the enterprise, and/or to specific individuals such as the user's supervisor or coach alerting or notifying them of noncompliance.

Figure 8:
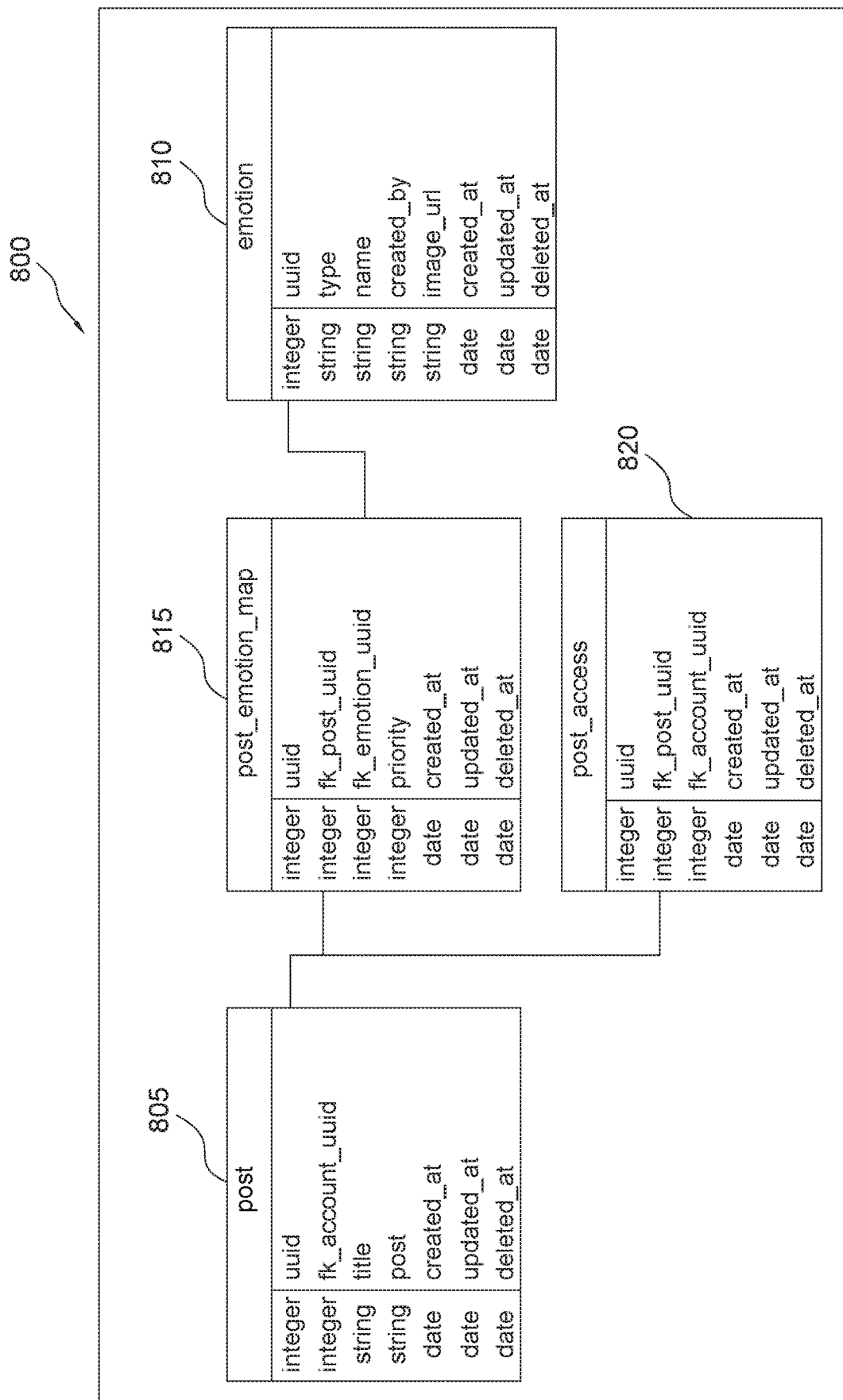
FIG. 8 depicts an illustrative implementation of the electronic message processing system in accordance with some embodiments of the present invention.

FIG. 8 depicts an illustrative implementation of the electronic message processing system 800 in accordance with some embodiments of the present invention. The processing system 800 is configured to store several electronic tables or data structures and to operate based on the electronic tables or data structures. In one embodiment, the processing system 800 includes a post-data structure 805 configured to communicate information in the message created through the emotion journaling application, an emotion icon data structure 810 configured to communicate emotion icon-related information, a post and emotion icon mapping data structure 815, and a post-access data structure 820.

The post-data structure 805 includes a post identifier that identifies the data structure or table 805 (uuid), a sender identifier that identifies the message sender (fk_account_uuid), title information (title), post information (post) that may include recipient selection information, emotion selection information, and text area content information (referring to the written content in the text area), and date information (created_at, updated_at, deleted_at). The title information refers to the title shown in 435 of FIG. 4A, which may be configured to a format of "Message—[Date of when the message was created]." The emotion selection information may include an instruction or an identifier identifying the emotion graphical representation (after the user makes the selection).

The processing system 800 may convert a message received from the emotion journaling application into a post-data structure 805 before further operation by the processing system 800. In some embodiments, the emotion journaling application may convert a message into a post-data structure 805 and then transmit that data structure to the processing system 800. In either situation, element 805 may also represent a database or storage device where all the messages or their data structures are stored. While FIG. 8 only shows one post-data structure 805, it is understood that the processing system 800 includes many post-data structures 805 or one database 805 storing many such post-data structures, as there are many employees in the company and each employee can send numerous messages to several recipients. The post identifier is a unique identifier that identifies a particular message or the data structure of that message. The post identifier may be generated by the processing system 800 or the emotion journaling application. In some embodiments, post data structure 805 or conversion to post data structure 805 may be necessary before the processing system 800 can perform other functions (e.g., before data structures 815 and 820 can retrieve relevant data from a message). Post-data structure 805 or the message before conversion includes the security token mentioned earlier in the application so that the processing system 800 can verify that the data structure or message is legitimate and should be processed, or make it accessible by data structures 815 and 820. If there is no security token, then the data structure or message is rejected by the processing system 800.

The emotion icon data structure 810 includes an emotion icon identifier that identifies the data structure or table 810 (uuid), a type identifier that identifies whether an emotion icon is positive or negative (type), the name of an emotion icon (name), information identifying who created the emotion icon if applicable (created_by), emotion icon location information (image_url), and date information (created_at, updated_at, deleted_at). Emotion icon location information may have information indicating where an emotion icon is stored, such as where it is stored in the processing system 800 or where it is stored outside the processing system 800 if the processing system accesses a database storing emotion icons outside the processing system 800. In some embodiments, emotion icon data structure 810 or conversion to emotion icon data structure 810 may be necessary before the processing system 800 can perform other functions (e.g., before data structures 815 and 820 can retrieve relevant data from a message), if the emotion icons are obtained from a component outside the processing system 800. While FIG. 8 only shows one emotion icon data structure 810, it is understood that the processing system 800 includes many emotion data structures 810 or one database 810 storing many such emotion icon data structures, because the emotion journaling application provides many different emotion graphical representations for selection. In some embodiments, the type identifier may also include the positive numerical value or negative numerical value. The database 810 may also store all the emotion names and emotion graphical representations that are on the list 327 (FIG. 3c).

Emotion graphical representations are stored on a database of the processing system such as the table 810, and the emotion graphical representation identifier (from the post information of the data structure 805) allows the processing system to access or call a particular emotion graphical representation in the table 810 for display to the recipients. The data structure 815 can access the data structure 805 through the post identifier (fk_post_uuid) and the data structure 810 through the emotion icon identifier fk_emotion_uuid). Though that access, the mapping data structure 815 can map data in the data structure 805 with data in the data structure 810. This way, only one set of emotion graphical representations needs to be stored on the processing system 800 and the processing system 800 can make the selected emotion graphical representation available to the recipients by directing the selected emotion graphical representation to the recipients using the identifier (e.g., without actually transmitting the emoji image to the recipient).

The post and emotion icon mapping data structure 815 includes a mapping identifier that identifies the data structure or table 815 (uuid), a post identifier that identifies a particular data structure or message in the database 805 (fk_post_uuid), an emotion icon identifier that identifies a particular emotion graphical representation in the database 810 (fk_emotion_uuid), priority information that identifies the sequence in which emotion graphical representations are selected, which may be obtained from the post information (post) in the data structure 805, and date information. The data structure 815 can access the data structure 805 through the post identifier (fk_post_uuid) and the data structure 810 through the emotion icon identifier fk_emotion_uuid).

Upon receiving a message from the emotion journaling application or the corresponding data structure 805, the processing system 800 maps the message or data structure 805 to the database 810 (or vice versa) and determines the emotion graphical representations selected in the message and their emotion names. The processing system 800 performs this operation for every received message. The processing system 800 then categorizes all the emotion graphical representations based on the emotion names, aggregates all the emotion graphical representations that have the same emotion name, and determines a percentage for each emotion name based on the ratio between the number of graphical representations in that emotion name and the total number of all the graphical representations in all the emotion names. The pie diagram in FIG. 7 illustrates the result produced by this operation. The other two diagrams in FIG. 7 based on time may be produced by using the date information in the data structure 805 (created_at). In any of the diagrams in FIG. 7, the post information in the data structure 805 is removed or is otherwise made unavailable so that only the emotion information is shown. Also, in all of the diagrams in FIG. 7, the sender information is made unavailable (not shown in FIG. 7). The processing system 800 may have similar aggregate information from messages and produce other data results shown in the other diagrams in FIG. 7 and FIG. 6 (610 and 605).

The post-access data structure 820 includes a message access identifier that identifies the data structure or table 820 (uuid), a post identifier that identifies a particular data structure or message in the database 805 (fk_post_uuid), a recipient identifier that identifies the message recipient (fk_account_uuid) which is obtained from the data structure 805, and date information. Although the same "fk_account_uuid" is used in both data structures 805 and 820, "fk_account_uuid" in each data structure actually refers to different individuals.

Upon receiving a message from the emotion journaling application or the corresponding data structure 805, the processing system 800 uses the data structure 820 to make the message available to the selected recipients. The selected recipients are identified by the "fk_account_uuid" in the data structure 820. The message made available to the selected recipients is identified by "fk_pos_tuuid" in the data structure 820. Through the "fk_post_uuid" in the data structure 820, the selected recipients can see who sent the message, the title of the message, the post information (including the emotion graphical representations mapped or determined through the data structure 815), and the message sent/creation date. The processing system 800 is configured to allow only the selected recipients access the data structure 820 or the message provided via the data structure 820. Other individuals in the company do not have access to the data structure 820 or the message provided by that data structure.

It may be possible to secure the text entry data such that it is only accessible by way of emergency involving the use of a security code by one or more senior-level personnel (e.g., supervisor, manager, CEO, etc.)

Date information in each data structure 805, 810, 815, and 820 may include creation date information, update date information, and deletion date information. Creation date information includes information indicating when the message or data structure is created. Update date information includes information indicating when the message or data structure is updated or modified. The emotion journaling application and the processing system may be configured such that the message sender can go back and edit the message he already sent (e.g., changing previously selected emotion graphical representations, editing previously written content) and the administrator or technician operating the processing system 800 can change certain information in data structures 815, 820. Deletion date information includes information indicating when the message or data structure is "deleted" because the user has left the company (e.g., the employee resigns, retires, or is terminated). Deletion in this context means that the message or data structure is made unavailable to the selected recipients, that the message or data structure is still available to the selected recipients but their emotion selections are not considered in the group-wide or company-wide aggregation data, or that the message or data structure is made unavailable to the selected recipients and the emotion selections are not considered in the group-wide or company-wide aggregation data. The processing system 800 may achieve "deletion" by moving the messages or data structures of the former employee to a separate location that is not accessible by the data structures 815, 820. Deletion date may indicate the time on which those the messages or data structures are put into that location.

The processing system 800 is understood to include a post and emotion icon mapping subsystem (815, or a combination that includes 805, 815, and 810) and a post-access subsystem (e.g., 820, or a combination that includes 805 and 820).

The processing system is configured to separate emotion information from text content and in response to the emotion information, the processing system aggregates the emotion information for an employee or a group of employees (e.g., under a supervisor) and sends that aggregated report to the supervisor. This way the user can understand the "pulse" of the group from the aggregated report and anonymize data. Personal thoughts written by the user are secured by the electronic message processing application (stored in a database of the electronic message processing application) to be visible only to the sender and his selected recipients.

The system for the assessment of emotional state is configured to make the user send each message to at least one other person as a condition for using the emotion journaling application or having access to other apps, systems, databases, or resources.

The emotion journaling application is configured to allow the user to select different message recipients every time. For example, the user may select individuals A, B, and C as message recipients for the current message. Next time when the user composes another message, the user can select individuals D, E, and F or B, C, and D as message recipients for this message.

In the display screen, a region (of the mobile app or the emotion journaling app) of the screen is configured for the selection of emotions (e.g., dedicated solely to emotion selection) and, for example, this is positioned in a specific area distinct from the text entry area. For instance, as shown in FIG. 3a, it is positioned directly above the text entry area.

A trusted anonymous feature is implemented. The system is configured to work on the individual's personal smartphone and allows them to log in to the emotion journaling application from their smartphone based on the system verifying and authenticating them to be an employee at the enterprise. This then provides a security token authorizing the user to use the emotion journaling application on their smartphone. The communications for logging in and subsequent application use are configured to use the existing smartphone and available network capabilities, such as communicating over a public network such as the Internet (e.g., as opposed to limiting communications within the private network of the enterprise). The ability to create a trusted environment for the user is one of the features provided by embodiments of the present invention. Through this feature, the user knows that his communications are secure and individuals on the system or have access to the system are not random people from the public. An example of authorization process and system for establishing a trusted environment is illustratively described in the attached application.

The emotion journaling application uses the local resources of the electronic device such as a smartphone to generate an interactive graphical user interface such as the illustrations described here (e.g., screen 300).

When an email message is automatically generated by the system for the assessment of emotional state comprising the message created by the emotion journaling application or substantially all such content, the message is automatically sent to selected recipients to their email address. The recipient can respond via email to the sender, whose address is specified to be the sender by the system for the assessment of emotional state. The parties can engage in an email dialogue external to the emotion journaling application and supporting system.

The separate data structures allow the system to apply different security settings to the different data, such as by separating named emotions from the text entry.

The system for the assessment of emotional state is distinct from employee evaluation systems, feedback systems, and other HR systems of the enterprise. The system for the assessment of emotional state is preferably a standalone system directed to provide functions described in this application. The system for the assessment of emotional state is preferably an additional system that the user can access from its own dedicated icon or link and does not incorporate or include employee review features or feedback features.

The individual may have a trusted group or a partner that is his work coach or confidant, and the system for the assessment of emotional state is configured to allow the individual to send his thoughts to that person via the emotion journaling application, but the processing system further uses and aggregates the names, emotions and related information (but not the text content) and makes that available or sends it to others, such as authorized managers or supervisors, to view group, company, and/or divisional level emotional state currently and over time.

The emotion journaling software application may also be a coaching software application. The coaching software application provides employee with a platform for "mental workout." Employees can get mentally fit by practicing, defining, describing, and exploring their emotions, good and bad. The coaching software application allows the user to share his thoughts and emotion with the people he trusts, such as coaches, peers, and colleagues. By sharing, it allows the coaches to understand the truth and mood of the individual and provide the right advice and suggestions. The coaching software application provides a secure and trusted environment, both considered objectively and subjectively by users and the system, as implemented, also provides immediacy (objectively and subjectively) such as the sender's message is immediately available and viewable (and the recipient is immediately notified using app notification).

A cloud computing platform such as Amazon Web Services ("AWS") may be used as part of the system for the assessment of emotional state. The user authentication system, the electronic message processing system, and/or some operations of the emotion journaling application may be implemented on such a platform. For example, emotion journaling applications may transmit messages to the electronic message processing system implemented on the AWS, and that AWS system may make messages and aggregated information available to the recipients and emotion journaling applications. In some embodiments, the electronic message processing system is a server-implemented system (e.g., cloud-based system) that functions to provide the features and services in conjunction with an emotion journaling application. Variations are also contemplated.

The user authentication system and the electronic message processing system include a user authentication software application or service and an electronic message processing software application or service, respectively, that configure the corresponding system to operate in the manners described above.

The electronic device may be a desktop computer, laptop computer, a tablet computer, a cellular device, a mobile device, a smartphone, a personal digital assistant ("PDA"), or other computer system having a microprocessor and memory. The electronic device is preferably a mobile smartphone that is handheld and capable of downloading and installing mobile applications that can communicate through the mobile phone with servers via mobile networks or other wireless networks. The electronic message processing system and the user authentication system, in some embodiments, are server-implemented systems (e.g., a cloud-based system) that functions to provide the features and services in conjunction with the electronic device or emotion recording application. Each of the electronic devices, systems, and servers is a computer system that includes a microprocessor and volatile and non-volatile memory to configure the computer system (using a software application such as one or more described herein). The computer system also includes a network connection interface that allows the computer system to communicate with another computer system over a network. The computer system further includes non-transitory storage devices such as a hard-drive, solid state drive, flash memory, permanent memory such as ROM, magnetic, optical, semiconductor, or any other suitable type of storage component, or any combination thereof that are configured to store data.

A server may have larger memory and larger storage capacity than those of an electronic device and has the capability of sustaining concurrent data communications with multiple end users or client devices. An electronic device may be a client device. In FIG. 1, the electronic device 105 may be a client device and the electronic message processing system 110 and user authentication system 115 may be implemented on a server (on the same server or separate servers). The employee database 120 may be implemented on electronic non-transitory storage devices such as those described above. The employee database 120 may also be an existing database in the enterprise or that is on the enterprise's internal network.

The communications network can include the internet, a cellular network, a telephone network, a computer network, a packet switching network, a line switching network, a global area network, a local area network ("LAN"), a wide area network ("WAN"), any number of private networks currently referred to as intranets, and/or any other network or combination of networks that can accommodate data communication. Such networks may be implemented with any number of hardware and software components, transmission media, and network protocols. Although FIG. 1 represents the network as a single network, the network can include multiple interconnected networks listed above.

In some embodiments, the electronic device on which the emotion recording application is implemented is connected to the electronic message processing system, user authentication system, and the database through WiFi, cellular network, and/or the internet to provide functionality and work with their supporting servers and storage devices. The electronic device does not, for example, use the company's local enterprise network (e.g., intranet) to communicate with the electronic message processing system, user authentication system, and the database or their supporting servers.

Data structure refers to computer data structure that allows computer systems, server, and electronic devices to access relevant data and operate based on accessed data. Data structure also refers to computer data structure configured to storing data in a particular manner or storing certain types of data.

It is understood from the above description that the functionality and features of the systems, devices, or methods of embodiments of the present invention include generating and sending signals to accomplish the actions.

It should be understood that variations, clarifications, or modifications are contemplated. Applications of the technology to other fields are also contemplated.

Exemplary systems, devices, and methods are described for illustrative purposes. Further, since numerous modifications and changes will readily be apparent to those having ordinary skill in the art, it is not desired to limit the invention to the exact constructions as demonstrated in this disclosure. Accordingly, all suitable modifications and equivalents may fall within the scope of the invention.

Thus, for example, any sequence and/or temporal order of steps of various processes or methods (or sequence of device connections or operation) that are described herein are illustrative and should not be interpreted as being restrictive. Accordingly, it should be understood that although the steps of various processes, methods, connections, or sequence of operations may be shown and described as being in a sequence or temporal order, they are not necessarily limited to being carried out in any particular sequence or order. For example, the steps in such processes or methods generally may be carried out in various different sequences and orders, while still falling within the scope of the present invention. Moreover, in some discussions, it would be evident to those of ordinary skill in the art that a subsequent action, process, or feature is in response to an earlier action, process, or feature.

It is also implicit and understood that the applications or systems illustratively described herein provide computer-implemented functionality that automatically performs a process or process steps unless the description explicitly describes user intervention or manual operation.

It should be understood that claims that include fewer limitations, broader claims, such as claims that do not require a certain feature or process step in the appended claim or in the specification, clarifications to the claim elements, different combinations, alternative implementations based on the specification, and different uses are also contemplated by the embodiments of the present invention.

It should be understood that combinations of described features or steps are contemplated even if they are not directly described together or not in the same context.

The terms or words that are used herein are directed to those of ordinary skill in the art in this field of technology and the meaning of those terms or words will be understood from terminology used in that field or can be reasonably interpreted based on the plain English meaning of the words in conjunction with knowledge in this field of technology. This includes an understanding of implicit features that for example may involve multiple possibilities, but to a person of ordinary skill in the art a reasonable or primary understanding or meaning is understood.

Software applications can be implemented as distinct modules or can be integrated together into an overall application such as one that includes the user interface and that handles other features for providing functionality to the user on his device.

It is intended that the specification and examples be considered as exemplary only, with a true scope being indicated by the claims and their equivalents.

The invention claimed is:

1. A system for assessment of emotional state comprising:
a non-transitory computer readable medium storing an emotion journaling application that causes a computer device to execute a method, the method comprising:
communicating with a database storing a list of names that part of an enterprise and obtain the list of names;
providing a user interface configured to allow creation of an electronic message, wherein the user interface is configured to:
allow selection of a message recipient from the list of employee names;
provide a list of emotion graphical representations;
allow selection of one or more emotion graphical representations or an odd number of emotion graphical representations greater than three from the list of emotion graphical representations;
provide a text area allowing a user of the computer device to input an entry in his or her own words;
make an electronic message transmittable to an electronic message processing system or the selected recipient when at least one message recipient has been selected, one or more emotion graphical representations have been selected, and a text entry has been inputted; and
make an electronic message available to the selected recipient, wherein the selected recipient can access the electronic message through an emotion journaling application on his or her computer device mobile device;
an electronic message processing system configured to receive messages created through the user interface and messages created through the user interfaces of the computer devices with the emotion journaling application, the electronic message processing system comprising:
a post data structure configured to convey information in the created message;
an emotion icon data structure configured to convey emotion icon-related information;
a post and emotion mapping data structure configured to convey emotional state information based information in the post-data structure and information in the emotion-icon data structure, wherein the emotional state information is communicated to the computer device and used by the emotion journaling application to present individual, group-wide, or company-wide emotional state information over a period of time; and
a post-access data structure configured to make the electronic message available to the elected recipients based on information in the post-data structure, wherein the post-access data structure is used by recipient's emotion journaling application to make the electronic message available to the selected recipient.

2. The system of claim 1, wherein the emotion graphical representations include a group of positive emotion graphical representations and a group of negative emotion graphical representations, wherein each representation in the positive group is associated with a positive numerical value and each representation in the negative group is associated with an equivalent negative numerical value.

3. A non-transitory computer readable medium storing an emotion journaling application that causes a computer system including a mobile device to execute a method, the method comprising:
providing a user interface configured to allow creation of an electronic message, wherein the providing comprising:
allowing selection of a message recipient from a list of individual names of an enterprise;
providing a list of emotion graphical representations;
allowing selection of one or more emotion graphical representations;
providing a text area allowing user of the mobile device input an entry in his own words;
making an electronic message transmittable to an electronic message processing system or the selected recipient when at least one message recipient has been selected, three or more emotion graphical representations have been selected, and a text entry has been inputted; and
making an electronic message available to the selected recipient, wherein the selected recipient can access the electronic message through an emotion journaling application on his mobile device; and
presenting individual, group-wide, or company-wide emotional state information over a period of time that includes the three selections of emotion graphical representations in the messages.

4. The non-transitory computer medium of claim 3, wherein the method further comprising:
providing an electronic message processing system configured to receive messages created through the user interface, wherein the providing comprising:
implementing a post and emotion mapping data structure configured to convey emotional state information based on information in a database storing electronic messages created through the user interface and information in a database storing emotion icons, wherein the emotional state information is communicated to the mobile device and used to present individual, group-wide, or company-wide emotional state information over a period of time; and
implementing a post access data structure configured to make the electronic message available to the selected recipients based on information in the database storing electronic messages created through the user interface, wherein the post access data structure is used by recipient's emotion journaling application to make the electronic message available to the selected recipient.

5. The system of claim 3, wherein the emotion graphical representations include a group of positive emotion graphical representations and a group of negative emotion graphical representations, wherein each representation in the positive group is associated with a positive numerical value and each representation in the negative group is associated with an equivalent negative numerical value.

6. A computer-implemented method comprising:
communicating with a database storing a list of individual names that are part of enterprise and obtain the list of names;
providing a user interface configured to allow creation of an electronic message, wherein the user interface is configured to:
  allow selection of a message recipient from the list of names;
  provide a list of emotion graphical representations;
  allow selection of one or more emotion graphical representations or an odd number of emotion graphical representations greater than three from the list of emotion graphical representations;
  provide a text area allowing a user of the mobile device to input an entry in his own words;
  make an electronic message transmittable to an electronic message processing system or the selected recipient when at least one message recipient has been selected, one or more of the emotion graphical representations have been selected, and a text entry has been inputted;
  make an electronic message available to the selected recipient, wherein the selected recipient can access the electronic message through an emotion journaling application on his mobile device; and
  present individual, group-wide, or company-wide emotional state information over a period of time based on messages created through the user interface and messages created through user interfaces of the other mobile devices with the emotion journaling application;
communicating with or establishing a system including:
  a post data structure configured to convey information in the created message;
  an emotion icon data structure configured to convey emotion icon-related information;
  a post and emotion mapping data structure configured to convey emotional state information based information in the post-data structure and information in the emotion-icon data structure, wherein the emotional state information is communicated to the mobile device and used by the emotion journaling application to present individual, group-wide, and company-wide emotional state information over a period of time; and
  a post-access data structure configured to make the electronic message available to the selected recipients based on information in the post-data structure, wherein the post-access data structure is used by recipient's emotion journaling application to make the electronic message available to the selected recipient.

\* \* \* \* \*